United States Patent [19]

Durham et al.

[11] Patent Number: 4,835,824
[45] Date of Patent: Jun. 6, 1989

[54] MEDICAL CLAMP

[76] Inventors: Vaughn L. Durham, 41 Trumbull Rd., Waterford, Conn. 06385; Jeffrey S. Goldblatt, 18 Huntington La., Norwich, Conn. 06360

[21] Appl. No.: 181,093

[22] Filed: Apr. 13, 1988

[51] Int. Cl.$^4$ .................... A61B 17/12; A44B 21/00
[52] U.S. Cl. ........................... 24/339; 24/346; 24/562; 128/346
[58] Field of Search ............. 24/339, 336, 543, 562; 128/346, 0.15

[56] References Cited

U.S. PATENT DOCUMENTS

| D. 234,204 | 1/1975 | Miller et al. . | |
|---|---|---|---|
| D. 235,127 | 5/1975 | Grant . | |
| D. 268,523 | 4/1983 | Scanlon, Jr. et al. . | |
| D. 276,461 | 11/1984 | Scanlon, Jr. et al. . | |
| 2,213,376 | 9/1940 | Bauer . | |
| 2,471,141 | 5/1949 | Castelli | 24/562 |
| 3,043,902 | 7/1962 | Klein . | |
| 3,060,536 | 10/1962 | LaVoie . | |
| 3,461,876 | 8/1969 | Miller, Jr. . | |
| 3,604,071 | 9/1971 | Reimels . | |
| 3,604,425 | 9/1971 | Le Roy . | |
| 3,616,497 | 11/1971 | Esposito, Jr. | 128/346 |
| 3,665,563 | 5/1972 | Batts . | |
| 3,698,043 | 10/1972 | Batts . | |
| 3,745,616 | 7/1973 | Batts . | |
| 3,777,760 | 12/1973 | Essner . | |
| 3,805,792 | 4/1974 | Cogley . | |
| 3,809,094 | 5/1974 | Cook . | |
| 3,809,371 | 5/1974 | Martini . | |
| 3,982,307 | 9/1976 | Smith et al. . | |
| 4,112,944 | 9/1978 | Williams . | |
| 4,193,174 | 3/1980 | Stephens . | |
| 4,212,303 | 7/1980 | Nolan | 24/543 |
| 4,227,730 | 10/1980 | Alexander et al. . | |
| 4,337,774 | 7/1982 | Perlin . | |
| 4,449,531 | 5/1984 | Cerwin et al. | 128/346 |

Primary Examiner—Victor N. Sakran
Attorney, Agent, or Firm—Chilton, Alix & Van Kirk

[57] ABSTRACT

A medical clamp (14) formed from a unitary, molded plastic strip (10) folded at its midpoint (12) into a generally "C" shape. Each leg (16, 18) has a base portion (20, 24) and an angled jaws portion (22, 26). A bar (42) extends from one base portion toward the other base portion (24), where, in the assembled clamp, it interengages another bar (44). Pincer members (28, 29) at the ends of the jaw portions have teeth (30) for securing the clamp to a sheet (35) or similar support surface on the operating table. One of the pincer members includes at its rear portion facing the midpoint of the strip, a wedge-like member (84), projecting substantially transverse to the leg. The other pincer member includes a ledge portion (86) acting as a stop surface adapted to received the wedge member in sliding interference fit as the jaws are closed. The interferece fit of the ledge portion and the wedge member limits the movement of one jaw relative to the other in a direction parallel to the legs, as the jaws are closed. The interaction of the wedge member and ledge in effect resists the tendency of one leg to move parallel relative to the other as the bars with hook (48) and retainer member (46) interengage for the purpose of locking the jaws together.

18 Claims, 2 Drawing Sheets

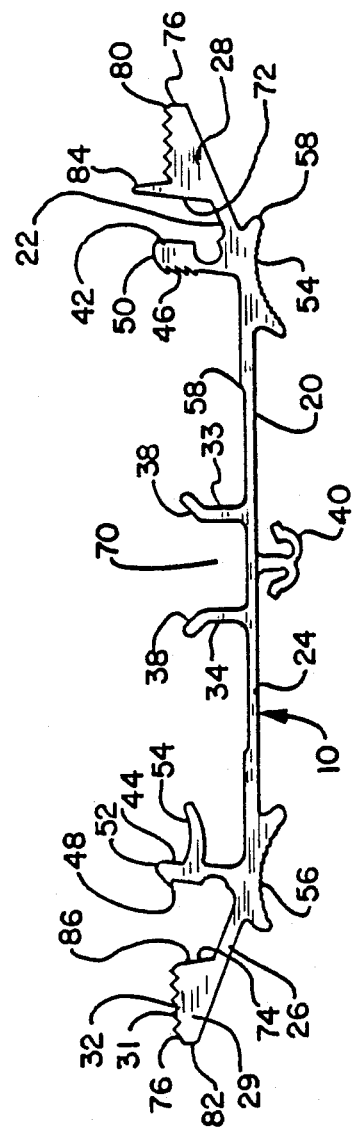
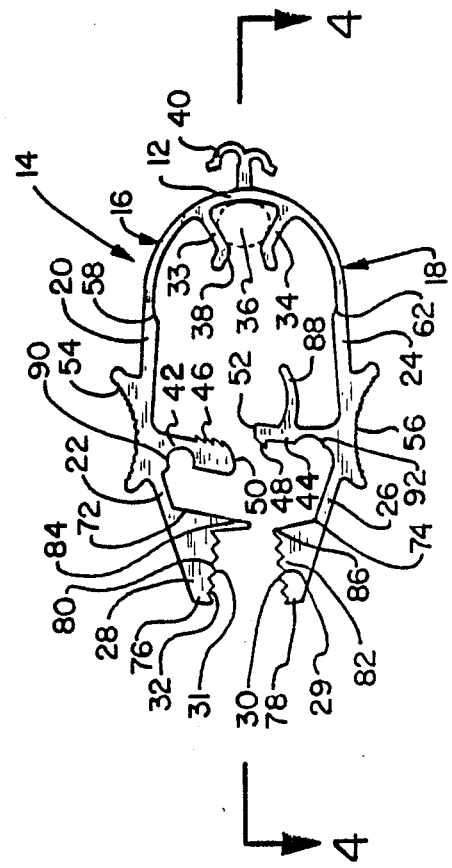
Fig. 1
Fig. 2

MEDICAL CLAMP

BACKGROUND OF THE INVENTION

The present invention relates to a clamping device, and particularly to a clamping device suitable for securing flexible lines during surgery.

A common problem during surgery is the handling and positioning of the many flexible lines that are required to carry fluids or electrical power to the patient and the surgical devices and equipment. Such lines may carry gases, such as oxygen, or fluids, such as blood or plasma, or consist of electrical cables for monitoring the patient. Often, the lines are desirably clamped to a support surface to keep the lines away from the operative site and to avoid entanglement.

SUMMARY OF THE INVENTION

In accordance with the present invention, a unitary, molded plastic strip having a plurality of projections, is folded about its midpoint to form a caliper-like clamp that is easy to use in the surgical theater yet can be fabricated so inexpensively that it is economically disposable after a single use.

After folding, the strip forms two legs, each having a base portion and a jaw portion extending therefrom, the base portions being spaced apart and the jaw portions being angled toward each other to form pincers. A bar projects from one of the legs toward the other, and has a hooked free end that is selectively engageable with a retainer member on another bar projecting from the other leg. Tabs project inwardly from the strip between the bars and the midpoint of the strip, for holding one or more tubes or lines. Pincer members at the ends of the jaw portions have teeth for securing the clamp to a sheet or similar support surface on the operating table.

One of the pincer members includes at its rear portion facing the midpoint of the strip, a wedge-like member, projecting substantially transverse to the leg. The other pincer member includes a ledge portion acting as a stop surface adapted to received the wedge member in sliding interference fit as the jaws are closed. The interference fit of the ledge portion and the wedge member limits the movement of one jaw relative to the other in a direction parallel to the legs, as the jaws are closed. The interaction of the wedge member and ledge in effect resists the tendency of one leg to move parallel relative to the other as the bars with hook and retainer member interengage each other for the purpose of locking the jaws together.

In a first position of operation, the hooked bar is disengaged relative to the bar with retaining member, so that the legs can be separated sufficiently for a tube or the like to be easily be inserted between the holding tabs. When the legs return to their neutral orientation corresponding to the second position of operation, the holding tabs move closer together and bias the tabs against the tube wall so that the clamp does not slide therein. Prior to surgery, one or more such clamps can be applied to every line or tube that is to be used during surgery, thus avoiding the need to connect the clamps to the lines during the course of the surgery. In a third position of operation, the legs are then grasped adjacent the bars and the bars are pushed toward each other until the pincer members bear upon a sheet or the like and the retaining member engages the hook. Preferably, the pincer force can be increased by securing the hook to different positions on the retainer member.

A release tab is preferably located on the bar which, when interengaged with the other bar, is closer to the clamp midpoint, such that by pivoting the release tab, the associated bar is drawn away from the other bar. The prestressed legs of the clamp spring away from each other slightly to the second position, releasing the sheet or the like from the pincer members, but preferably continuing to retain the lines between the holding tabs.

BRIEF DESCRIPTION OF THE DRAWINGS

FIG. 1 is a top view of a molded plastic strip, lying on edge, showing the various structures constituting the medical clamp of the present invention;

FIG. 2 is a side view of the strip illustrated in FIG. 1, curved about its midpoint to form a clamp with a tube retained between the holding tabs prior to full closure of the clamp;

DESCRIPTION OF THE PREFERRED EMBODIMENT

Figure 3:
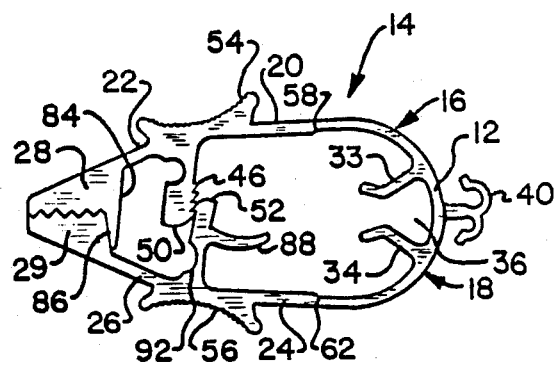
FIG. 3 is a view similar to FIG. 2 after the clamp has been closed.

FIGS. 1-3 show a unitary, molded plastic strip 10 that is curved about its mid or center point 12 into a generally "C" shaped clamp 14. The strip 10 can be made from a variety of plastic materials, so long as the strip 10 is flexible or resilient enough to assume the position shown in the Figures, without cracking or breaking. Preferably, the strip is molded with an inherent curvature at the midpoint 12, so that when lying on an edge in the disassembled condition, it assumes a "C" shape, such as shown in FIG. 2.

The clamp 14 has a first leg 16 and a second leg 18 which for convenience will hereinafter be referred to as the upper leg 16 and lower leg 18. A similar directionality will be used in referring to structures carried by these legs. The upper leg 16 includes a base portion 20 and a jaw portion 22, which are opposite and generally symmetric to the lower base portion 24 and lower jaw portion 26 relative to an imaginary plane passing through center point 12. The pincer members or structures 28, 29 of the respective jaws 22, 26 each have a plurality of teeth 30 which are formed by parallel alternating ridges and grooves 31, 32 for attachment to a sheet or the like.

At the interior near the mid point 12, the clmap has upper and lower holder tabs 33, 34, respectively, which are sized and oriented to engage and resiliently apply pressure upon the side wall of a tube 36 or the like (shown in phantom). At least one tab 33, 34 can be angled to facilitate the insertion and retention of a tube 36 by means of the slight resistance to passage between the corners of the angles 38. A hook 40 may also be provided externally at the midpoint 12.

The strip 10 is originally molded so that it has inherent tendency for the legs to assume a neutral position such that the pincer members 28, 29 remain separated. In order to maintain the teeth 30 in overlapping relation when the pincer structure 28, 29 is connected to a support (not shown), the upper leg 16 must be restrained from pulling away from the lower leg 18. This is accomplished with the present invention by providing a first bar 44 projection downwardly from the upper leg 16, and a second bar 42 projection upwardly from the lower leg 18, each bar having a hooked, notched, or pawl-like structure 46, 48 for selective interengagement whereby the upper and lower legs 16, 18 are held in the desired spacing againt the biasing force inherent at the midpoint 12. Preferably, in the engaged condition shown in FIG. 3, the base portions 20, 24 of the legs are substantially parallel, whereas the jaw portions 22, 26 extend obliquely toward each other such that the teeth thereof overlap, i.e., the ridges and grooves 31, 32 of one pincer member 28 contact the grooves and ridges of the other pincer member 29, in the imaginary plane passing through midpoint 12.

Figure 4:
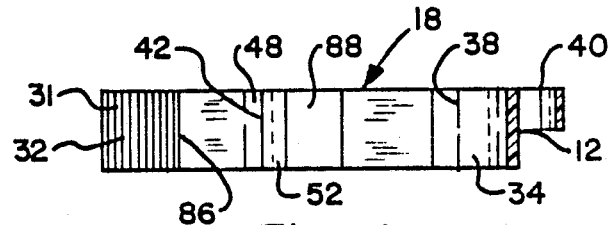
FIG. 4 is a section view of the clamp taken along line 4—4 of FIG. 2.

As shown in FIGS. 1, 2, and 4, the upper and lower bars 42, 44 are preferably the same width as the strip 10. The notches 46 are provided in the form of a rack having teeth oriented transversely to the strip 10 and facing the midpoint 12. The hook 48 on the lower bar 44 is angled toward the rack 46 for engagement therewith. The free end 50 of the upper bar 42 and the free end 52 of the lower bar 44, are curved to provide a cam-like relative sliding to guide the hook 48 toward the rack 46 as the bars 42, 44 are urged toward each other.

The clamp 14 is closed by grasping it in the hand with the thumb on the thumb piece 54 and pivoting the legs toward each other about the center point 12. The thumb piece is formed at the juncture of the jaw portion 22 and the upper base 20, at a location approximately where the upper bar 42 projects downwardly from the leg and preferably is of concave shape. The forefinger is placed on the finger piece 56, similarly located with respect to the lower base 24. Downward pressure applied by the thumb on the thumbpiece 54 causes the rack 46 to advance downwardly relative to the hook 48. This pressure on the thumbpiece 54 produces a force component which tends to advance upper pincer member 28 forward relative to lower pincer member 29 and, if not counteracted as described below, can cause the interengaged teeth 30 to "climb" over each other and prevent tight closure.

Figure 5:
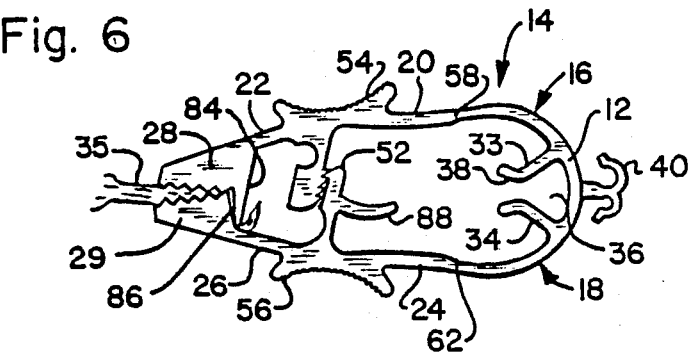
FIG. 5 is a view similar to FIG. 3, showing the attachment of the clamp to a sheet with a tighter closure than shown in FIG. 3.

FIG. 5 shows the position of the clamp 14, during manual actuation to close the jaws 22, 26 even tighter than shown in FIG. 3. During such further tightening of the jaws, and typically when a thick sheet 35 or the like is secured, the rear portion of the clamp 14 is somewhat deformed but the holding bias of the tabs 33, 34 against the tube 36 is not diminished.

The thumb and finger pieces 54, 56 are preferably knurled on their exterior surfaces to provide a more secure grip to the user. Also, to facilitate the deformation of the clamp 14 as between the shapes shown in FIGS. 3 and 5, flex zones 58, 62 are provided immediately behind the thumb and finger pieces 54, 56 by molding the strip 10 with a smaller thickness.

Each jaw portion 22, 26 has at its end remote from the center point 12, an enlarged pincer member 28, 29, each having a rear portion 72, 74 facing the centerpoint 12, a front portion 76, 78 facing away from the centerpoint, and an intermediate portion 80, 82 on which are formed the plurality of teeth 30, preferably saw-toothed. The rear portion 72 of one pincer member 28 includes a wedge member 84 projecting toward the other pincer member 29 and the rear portion 74 of the other pincer member 29 includes a ledge portion 86 adapted to receive the wedge member 84 in sliding interference fit as the jaws are closed.

As indicated in FIG. 4, the wedge member 84 and ledge portion 86 have substantially the same width as the respective jaws 22, 26. The ledge portion and wedge member are positionally related such that they first contact at approximately the same moment that the cammed surfaces 50, 52 of the bar members 42, 44 contact during closure of the clamp. The ledge portion 86 can include a slight bend toward the midpoint 12 in the vicinity of the rear most tooth, to facilitate such substantially simultaneous contact. Preferably, at this initial contact of the wedge member 84 and ledge portion 86, the teeth 30 are not interengaged in contact, but upon engagement of the hook 48 with the first tooth of rack 46, the ridges 31 of the teeth on one pincer member 28 are in mating engagement with the grooves 32 in the pincer member 29 of the other jaw. This initial closure position is shown in FIG. 3. In this closure position as illustrated the wedge member 84 and the ledge portion 86 form substantially the same angle relative to the imaginary central plane.

Upon further pressure by the user's fingers on the legs 16, 18 toward each other, the hook 48 engages increasingly higher notches in the rack 46. Although the clamp 14 is deformed somewhat, whereby some teeth may become separated, the wedge member 84 is quite strongly urged against the ledge portion 86, such that a sheet or the like cannot easily slip from the grasp of the pincer members 28, 29.

Regardless of the clamping force dictated by the particular notch engaged by the hook 48, rapid and reliable release of the clamping action can be obtained by applying a slight downward pressure on the release tab 88, which projects from the lower bar 44 and thus pivots the bar 42 away from the notches of the rack 46. This disengages the hook 48 from the rack 46, and the natural prestresses in the strip 10 due to the formation of the initial bending into the general "C" shape, produces a spring-back to the position shown in FIG. 2.

Figure 6:
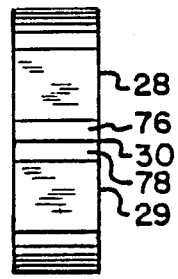
FIG. 6 is a front end view of the clamp shown in FIG. 3.
Figure 7:
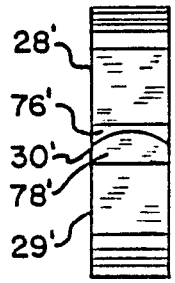
FIG. 7 is an end view showing an alternative embodiment of the front end.

Certain details may advantageously be incorporated to optimize performance of the clamp. For example, the upper bar 42 and the lower bar 44 both have cut-out regions 90, 92 near the legs 16, 18 and towards the pincer members 28, 29 for the purpose of optimizing the resiliency of the interaction between the hook 48 and the rack 46 and the pressure needed to disengage the hook 48 by means of the release tab 88. The pincer members 28, 29, which have planar toothed surfaces 30 as shown in the end view of FIG. 6 could alternatively have mating concave and convex surfaces 30' formed on pincer members 28', 29' as shown by the end view of front portions 76', 78' in FIG. 7. This further stabilizes the jaws laterally during closure.

It should be appreciated that the present invention is well adapted to improve upon known clamps, by providing the function of stabilizing the jaws during closure, so that the hook 48 and rack 46 on the respective bars 44, 42 remain sufficiently biased toward each other during closure to permit sequential positive engagement of the hook 48 with the notches on the rack 46, while at least a portion of the pincer members 28, 29 forcefully engage the support material, particularly a sheet, to which the clamp 14 is intended to be attached.

With reference now to FIGS. 1–3, the operation of the clamp 14 will be described. In an advantageous use of the invention, the clamp 14 is available to the surgical team in an initial condition having the shape shown in FIG. 2. Regardless of the exact initial configuration, the strip 10 is rather flexible and thus can be manipulated so as to provide an opening 70 between the holding tabs 33, 34 that is large enough to pass one or more lines or tubes 36, toward the midpoint. The user then grasps the clamp 14 with the thumb and the forefinger substantially on the thumb and finger pieces 54, 56 and squeezes the jaws and base portions toward each other. The complementary exterior surfaces of the free ends 50, 52 on upper and lower bars 42, 44 come into contact and slide obliquely relative to each other until the hook 48 on the lower bar engages the rack on the upper bar. As the hook 48 slides upwardly along the lowermost notch on the rack 46, the wedge member 84 contacts and slides along the ledge portion 86, thereby preventing the teeth on pincer member 28 from moving forward along the midplane relative to the teeth on pincer member 29. This also has the effect of preventing the rack 46 from moving too far forward, away from the hook 48, and thus assures engagement and stability during further tightening.

During the preparatory stages of the surgery, every line 36 to be utilized during the surgery is secured between tabs 33, 34 on one or more clamps 14. As each line is needed during surgery, it can be fastened by means of the thumb and finger pieces 54, 56 and jaws 22, 26 to sheets or other support surfaces. Especially with the angled tabs 33, 34, once the tube 36 has been initially secured, in the configuration shown in FIG. 2, the subsequent opening and closing of the jaws does not significantly loosen the holding pressure between the tabs and the tube. Optionally, during surgery one or more clamps 14 can be opened from the configuration of FIG. 2 to a configuration approaching that of FIG. 1 if it is desired to remove certain tubes 36 and replace then with other tubes. Or, preferably, the angled tabs 33, 34 are used whereby the resilient threshold produced by corners 38 can be overcome while either inserting or removing a tube 36 regardless of the configuration of the clamp 14. The tabs 33, 34 thus form an open-sided cradle.

It should be appreciated by those familiar with the surgical theater that the present invention is well-suited to serve the needs of the surgical team, insofar as supporting and moving tubes is concerned. Moreover, the simple fabricating technique, in which the clamp is formed as a unitary, molded piece, reduces the unit cost to the point where the clamps are disposable after one use. This avoids the administrative and energy costs associated with the sterilization of reusable clamps.

What is claimed is:

1. A medical clamp comprising:
    a unitary plastic strip including two connected legs moveable toward each other about a center point, the legs forming opposed jaws for attachment to an object;
    each jaw having a pincer member including a toothed portion facing the toothed portion of the other jaw, and a rear portion facing the center point;
    the rear portion of one pincer member including a stop surface and the rear portion of the other pincer member including means projecting toward the stop surface for interacting with the stop surface to limit the movement of one pincer member relative to the other pincer member in a direction parallel to the legs as the legs are moved toward each other; and
    means for securing the legs together in a closed position while the projecting means interact with the stop surface.

2. The medical clamp of claim 1 wherein the toothed portions of the pincer members have ridges and grooves defining saw teeth adapted to interengage each other when the pincer members are brought into contact and the legs are secured to each other.

3. The medical clamp of claim 2 wherein the teeth on the pincer members are oriented transversely to the legs.

4. The medical clamp of claim 1 further including a tab member carried on each leg near the center point, the tab members together forming an open sided cradle for retaining a flexible tube when the legs are secured together.

5. The medical clamp of claim 4 wherein at least one tab is angled to form a resilient corner serving as a threshold for selectively permitting and preventing the passage of a tube into or out of the cradle.

6. The medical clamp of claim 1 wherein the stop surface is oriented in the direction from one leg to the other.

7. The medical clamp of claim 6 wherein the means projecting toward the stop surface include a wedge member adapted to slide along the stop surface as the legs are moved toward each other.

8. The medical clamp of claim 7 wherein the plastic strip has a uniform width and the stop surface and wedge member are the same width as the strip.

9. The medical clamp of claim 7 wherein the size and orientation of the wedge member relative to the stop surface are such that as the legs are moved closer together the interacting force between the wedge member and the stop surface increases.

10. The medical clamp of claim 1 wherein the means for securing the legs together include a first bar projecting from one leg toward the other leg and a second bar projecting from the other leg to said one leg, for interengaging to secure the legs in the closed position.

11. The medical clamp of claim 10 wherein the first bar includes a retainer member having a notched rack and the second bar includes a hook member oriented to engage the notched member as the legs are moved toward each other.

12. The medical clamp of claim 11 wherein the retainer member includes a first contoured surface and wherein the hook member includes a second contoured surface, the first and second contoured surfaces being oriented to contact each other as the legs are moved toward each other, for guiding the hook into the notched rack.

13. The medical clamp of claim 12 wherein when the contoured surfaces are in contact immediately before the hook engages the notched rack, the means projecting toward the stop surface contact the stop surface.

14. A medical clamp comprising:
    a unitary strip including first and second legs having curved portions connected substantially symmetrically about a center point, the legs forming opposed jaws for attachment to an object;
    each jaw having a pincer member including a rear portion facing the center point and a front portion facing away from the center point, each pincer member having between the rear and front portions, a plurality of teeth defined by alternating ridges and grooves oriented substantially parallel to each other and transverse to the legs;

the rear portion of one pincer member including a wedge member projecting toward the other pincer member, and the rear portion of the other pincer member including a ledge portion adapted to receive the wedge member in sliding interference fit as the jaws are closed, whereby the interference fit of the ledge portion and wedge member limits the movement of one jaw relative to the other in a direction parallel to the legs, as the jaws are closed; and first and second means projecting toward each other from the first and second legs respectively, for interengaging to secure the jaws in a closed position as manual pressure is applied to the legs to move the legs toward each other.

15. The medical clamp of claim 14, wherein the center point lies on an imaginary plane and the teeth of the jaws are symmetrically located above and below the plane such that when the jaws are closed against each other, the ridges on one jaw contact the grooves in the other jaw, in said plane.

16. The medical clamp of claim 15, wherein when the jaws are closed, the wedge member and the ledge portion form substantially the same angle relative to said plane.

17. The medical clamp of claim 14 wherein one pincer member has a convex surface containing said teeth and the other pincer member has a concave surface containing said teeth.

18. the medical clamp of claim 17 wherein the center point lies on an imaginary plane passing between the legs and when the jaws are closed, the wedge member and the ledge portion form substantially the same angle relative to said plane.

* * * * *